(12) United States Patent
Kopfer

(10) Patent No.: US 6,550,914 B1
(45) Date of Patent: Apr. 22, 2003

(54) EYEWEAR WITH FILTERED VENTILATION

(75) Inventor: Rudolph J. Kopfer, Belvedere, CA (US)

(73) Assignee: Pan-Optx, Inc., Pleasanton, CA (US)

(*) Notice: Subject to any disclaimer, the term of this patent is extended or adjusted under 35 U.S.C. 154(b) by 0 days.

(21) Appl. No.: 10/039,630

(22) Filed: Oct. 26, 2001

(51) Int. Cl.[7] .................................................. G02C 11/08
(52) U.S. Cl. ............................................. 351/62; 2/437
(58) Field of Search .......................... 351/158, 41, 62; 2/435, 436, 437, 438

(56) References Cited

U.S. PATENT DOCUMENTS

| | | | |
|---|---|---|---|
| RE12,924 E | 3/1909 | Cover | 351/41 |
| 1,031,859 A | 7/1912 | Malcom | 351/41 |
| 1,433,676 A | 10/1922 | Cover | 351/41 |
| 1,478,818 A | 12/1923 | Cover | 351/41 |
| 1,562,350 A | 11/1925 | Luckey | 351/41 |
| 1,669,229 A | 5/1928 | Cook | 351/41 |
| 1,677,747 A | 7/1928 | Cook | 351/41 |
| 1,720,814 A | 7/1929 | Baker | 351/41 |
| 1,741,427 A | 12/1929 | Meyrowitz | 351/41 |
| 1,754,694 A | 4/1930 | Neuwirth | 351/41 |
| 1,846,679 A | 2/1932 | Fischer | 351/41 |
| 1,853,872 A | 4/1932 | Meyrowitz | 2/14 |
| 1,936,746 A | 11/1933 | Baker | 2/14 |
| 1,989,876 A | 2/1935 | Meyrowitx | 2/14 |
| 2,002,543 A | 5/1935 | Meyrowitz | 2/14 |
| 2,007,186 A | 7/1935 | Farrell | 2/14 |
| 2,026,435 A | 12/1935 | Ratti | 2/14 |
| 2,321,159 A | 6/1943 | Ryan | 88/41 |
| 2,364,584 A | 12/1944 | Malcom | 2/14 |
| 2,387,821 A | 10/1945 | Baratelli et al. | 2/14 |
| 2,466,048 A | 4/1949 | Kimball | 2/14 |
| 2,526,181 A | 10/1950 | Wilen | 2/14 |
| 2,608,687 A | 9/1952 | Ellis | 2/14 |
| 2,846,684 A | 8/1958 | Hill | 2/14 |
| 3,377,626 A | 4/1968 | Smith | 2/14 |
| 3,419,909 A | 1/1969 | Spain | 2/174 |
| 3,556,644 A | 1/1971 | Stahl | 351/118 |
| 3,591,864 A | 7/1971 | Allsop | 2/14 |
| 4,405,212 A | 9/1983 | Cooper | 351/43 |

(List continued on next page.)

FOREIGN PATENT DOCUMENTS

| | | |
|---|---|---|
| FR | 321010 | 7/1902 |
| FR | 324973 | 10/1902 |
| FR | 2130907 | 11/1972 |
| GB | 127410 | 5/1918 |
| GB | 364970 | 2/1931 |
| JP | 56-133716 | 10/1981 |

Primary Examiner—Huy Mai
(74) Attorney, Agent, or Firm—Stroock & Stroock & Lavan LLP

(57) ABSTRACT

Eyewear is disclosed for use in sports and the like which captures airflow impinging on the front of the eyewear, filters it through baffling or a particulate filter to prevent the ingress of particulate matter, and then directs it through the dead space between the lenses and the wearer's eyes. The eyewear includes a frame shaped to fit a wearer's face including a front-facing ventilation opening, one or two lenses mounted in the frame, and a ventilation liner which includes filtered upper ventilation grooves extending through the top and bottom surface of the eyewear to allow air to flow through the dead space behind the lens. A cushion can be attached to the rear surface of the ventilation liner for cushioning the eyewear against the user's face.

24 Claims, 4 Drawing Sheets

U.S. PATENT DOCUMENTS

| | | | |
|---|---|---|---|
| 4,414,693 A | 11/1983 | Brody | 2/435 |
| 4,468,819 A | 9/1984 | Ohno | 351/43 |
| 4,544,245 A | 10/1985 | Stansbury, Jr. | 351/120 |
| 4,654,899 A | 4/1987 | Harris | 2/436 |
| 4,707,863 A | 11/1987 | McNeal | 2/436 |
| D293,504 S | 1/1988 | Specht et al. | D16/107 |
| D295,533 S | 5/1988 | Wichers | D16/102 |
| 4,741,611 A | 5/1988 | Burns | 351/44 |
| 4,785,481 A | 11/1988 | Palmer, III et al. | 2/436 |
| 4,792,221 A | 12/1988 | Parks et al. | 351/120 |
| 4,877,320 A | 10/1989 | Holden | 351/44 |
| 4,955,708 A | 9/1990 | Kahaney | 351/44 |
| 5,018,223 A | 5/1991 | Dawson et al. | 2/436 |
| 5,191,364 A | 3/1993 | Kopfer | 351/62 |
| D339,596 S | 9/1993 | Kopfer | D16/102 |
| 5,428,411 A | 6/1995 | Kopfer | 351/62 |
| 5,711,035 A * | 1/1998 | Haslbeck | 2/436 |
| D402,681 S | 12/1998 | MacWilliamson | D16/327 |
| 6,026,518 A * | 2/2000 | Brown | 2/439 |
| 6,076,196 A * | 6/2000 | Masumoto | 2/436 |
| D428,913 S | 8/2000 | Kopfer | D16/326 |
| 6,233,342 B1 | 5/2001 | Fernandez | 381/62 |

\* cited by examiner

EYEWEAR WITH FILTERED VENTILATION

TECHNICAL FIELD OF THE INVENTION

This invention relates generally to eyewear for use in sports and the like; and more particularly to eyewear which is ventilated to reduce or prevent fogging, increase comfort and protect from the wind.

BACKGROUND OF THE INVENTION

Eyewear used for sports is typically designed to wrap around the user's face and is sufficiently close to the skin to create a dead air space between the glasses and the user's face (hereinafter referred to as the "dead space"). As the user engages in strenuous activity, the heat and moisture can build up in the dead space, making the glasses uncomfortable to wear and producing condensation on the inside surface of the lenses which can partially or entirely obstruct the vision of the wearer. This phenomenon is commonly known as "fogging."

There have been many prior art methods attempted to reduce or eliminate fogging. Some devices, such as that described in U.S. Pat. No. 4,707,863, describe chemical coatings which can be applied to the inside surface of a lens to alleviate fogging. Such coatings, however, tend to enhance fingerprints caused by handling, and are typically not durable, tending to scratch and wear off when the user cleans the lenses.

Therefore, different types of ventilation have been relied upon to alleviate fogging. Many prior art sunglasses and protective glasses or goggles provide openings in the frame above and below the lenses to allow air to flow in and out. These are not believed to be particularly effective at preventing fogging when a wearer is engaged in particularly strenuous activity, since there is nothing to cause the air to actually flow through the dead space, unless the wearer tilts his head downward towards the ground as he is moving forward to allow the passing air to flow through the perforations in the frame. This is not particularly desirable when the wearer is moving forward at great speed (for example, when riding a motorcycle) because such action will take the wearer's eyes off the space in front of his vehicle and may result in an unfortunate accident. Moreover, open apertures will typically allow the ingress of dust and particulate matter into the dead space where it can be blown into the unprotected eyes by the flow of air, which is also very undesirable.

U.S. Pat. Nos. 5,191,364 and 5,428,411 substantially reduced or eliminated the ingress of dust and particulate matter into the dead space by covering the ventilation apertures with permeable foam, and further addressed the fogging problem with coated and/or double lenses. However, these glasses still suffer from the lack of a motivating force for causing a flow of air through the ventilating apertures without causing the wearer to take his eyes off his direction of travel. Moreover, when the wearer is no longer engaged in active sports, and wishes to simply wear a pair of casual sunglasses to protect the eyes from the effects of sunlight while walking or driving in a closed vehicle, the foam surrounding the eyes combined with decreased airflow may cause an uncomfortable heat build up which discourages the user from wearing such eyewear for casual purposes.

British Patent Specification 364,970 addressed the problem of controlling a flow of air through the dead space by providing a valve which may be adjusted by loosening a screw, rotating an inlet regulating disc to a desired position, and then tightening the screw. This device is not desirable because the user must remove the glasses, produce a screw driver, loosen the screw, rotate the disc, tighten the screw, put the glasses back on and use them at the desired speed to determine if the disc has been rotated to a position which will produce the desired flow under the specific conditions of use. If not, the procedure must be repeated over and over again until the desired flow is obtained.

Accordingly, the need exists for sunglasses and protective glasses which automatically generate a flow of filtered air through the dead space and protects the eyes from particulate matter in the airstream when the user is engaged in active sports.

SUMMARY OF THE INVENTION

In one embodiment, the present invention provides eyewear for use in sports and the like having a frame shaped to fit a wearer's face, the frame having an inner surface, an outer surface, a pair of orbital openings for surrounding the eyes of a wearer, a nose bridge connecting the orbital openings and having a filtered ventilation opening, a lens mounting surface mounting a lens over each orbital opening, and a surface on each side of the frame for attaching temple bars or a strap for supporting the frame on the wearer's head, and a ventilation liner having a pair of orbital openings connected by a nose bridge of substantially the same size and shape as the orbital openings and nose bridge of the frame, the ventilation liner including a front surface mounted to closely engage the inner surface of the frame, a rear surface, and a channel formed in the nose bridge of the ventilation liner for diverting airflow from the ventilation opening of the frame across an inner surface of each lens, the ventilation liner further including a plurality of filtered upper ventilation grooves across an upper portion of the front surface of each orbital opening of the ventilation liner and a plurality of filtered lower ventilation grooves across a lower portion of the front surface of each orbital opening of the ventilation liner, also for creating airflow across the inner surface of each lens, and a cushion covering said rear surface of said ventilation liner for engaging a wearer's skin around the eyes.

In another embodiment, the present invention provides eyewear including a frame shaped to fit a wearer's face having an inner surface, an outer surface, a lens mounting surface for mounting a lens for protecting a wearer's eyes, at least one lens mounted on said lens mounting surface, a nose bridge for supporting said frame on said wearer's face, a filtered ventilation opening through a front surface of said frame, and, a surface on each side of the frame for attaching temple bars or a strap for supporting the frame on the wearer's head, and a ventilation liner mounted to the inner surface of the frame, the ventilation liner having at least one eye aperture of substantially the same size and shape of the aperture formed by the lens mounting surface of the frame for forming a deadspace between the lens and the wearer's eyes, the ventilation liner further having a front surface closely engaging the inner surface of the frame and extending above a top surface of said frame, the front surface of the ventilation liner including a plurality of filtered upper and lower ventilation grooves, and a channel for directing a flow of air from the filtered ventilation opening in said frame into the deadspace, and said ventilation liner further including a cushion mounted across a rear surface of the ventilation liner for engaging a wearer's skin to seal the area around the wearer's eyes.

Other and further objects, features, advantages and embodiments of the present invention will become apparent

DETAILED DESCRIPTION OF THE INVENTION

Figure 1:
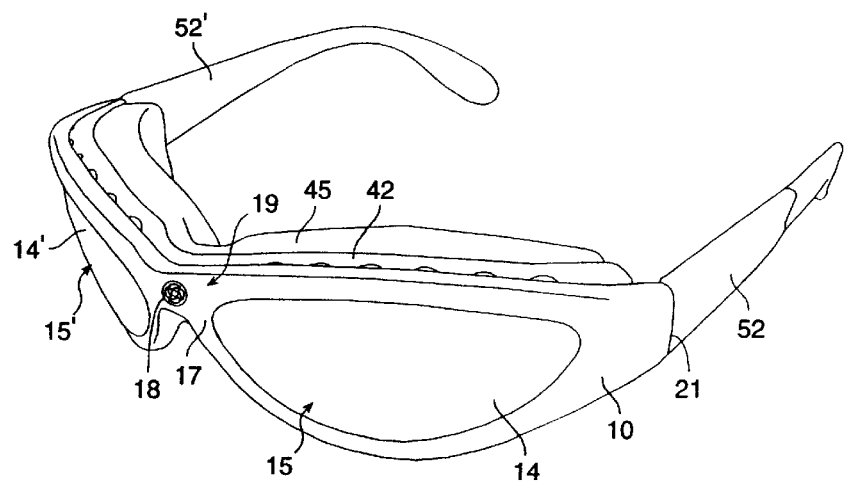
FIG. 1 is a perspective front view of eyewear of the present invention.

As shown in FIGS. 1–5, eyewear of the present invention includes a frame 10, which is preferably formed from a resilient material such as plastic. Metal frames, while less desirable, can also be used. The frame 10 includes an aperture for the eyes of the wearer which is circumscribed by a lens mounting surface 12, on which one or more lenses 14 are mounted.

Lenses 14, 14' are conventionally mounted to the lens mounting surface, and may be tinted or coated to provide protection against the rays of the sun, and/or may be corrective lenses to correct the vision of far-sighted or near-sighted wearers. Most preferably, the frames 10 are provided with two eye apertures, a right eye aperture 15' aligned with the wearer's right eye and a left eye aperture 15 aligned with the wearer's left eye. However, as shown in U.S. Pat. No. 6,233,342, which is incorporated herein by reference, the frame may also be constructed to provide a single aperture for both eyes, which is covered with a single lens.

Frame 10 is most preferably curved to closely fit against the wearer's face and to provide for substantially unobstructed peripheral vision. Frame 10 is also preferably provided with a nose bridge 17 to support the eyewear on the bridge of the user's nose. Nose bridge 17 provides a convenient location on the front surface of the frame 10 which can be perforated for ventilation if desired. In the preferred embodiment, shown in FIG. 1, a single ventilation opening 18 is provided which is covered on the outer surface 19 by a perforated vent cover 20. While less preferred, it would also be possible to place one or more ventilation openings at other locations on the front surface of the frame 10. While even less preferred, ventilation opening 18 may be omitted entirely.

Figure 8:
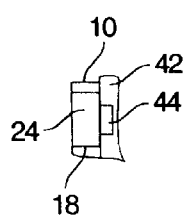
FIG. 8 is a partial cross-section taken through line 8—8 of FIG. 4.

The ventilation opening 18 is preferably filtered to prevent the ingress of particulate matter. Most preferably, a filtering element 24 (shown in FIG. 8) can be placed directly in the ventilation opening 18. Filter element 24 can be formed from any material capable of preventing the ingress of particulate matter without unduly obstructing the flow of air. Most preferably, filter element 24 is formed from air permeable foam placed inside the opening 18 for filtering the air as it passes through ventilation opening 18. If opening 18 is too small for a filtering element 24, it may be possible to place a filter element at a different location further downstream before the airstream enters the deadspace, such as, for example, in inlet channel 44. While not preferred, opening 18 can be left unfiltered if desired. The air which enters through opening 18 will encounter the wall in inlet channel 44, and be forced to turn 90 degrees before entering into the dead space, which should prevent most if not all windborne particulate matter from being blown into the eyes.

The inside of frame 10 is most preferably fitted with a ventilation liner 42 contoured to fit a wearer's face closely while spacing the lenses from the wearer's face to create a dead space 26 between the user's eyes and the lenses. Ventilation liner 42 can be constructed from the same material as the frame 10 and is provided with a front surface 43 which abuts the inside of frame 10, and a rear surface 44 which is preferably covered with a cushioning material 45 to comfortably seal the eyewear against the user's face and prevent the ingress of dust and particulate matter through the space between the periphery of the glasses and the user's face. The cushion 45 can be attached about the periphery of the rear surface 44 of ventilation liner 42, or cushion 45 can be formed as a gasket which wraps around the rear surface 44 starting at the top of the ventilation liner 42 and wrapping across the rear surface 44 to the bottom of the ventilation liner 42. Cushion 45 can be formed from any material suitable for both cushioning and providing an air permeable seal; however, air permeable foam is preferred. While far less preferable, ventilation liner 42 in its simplest form can be simply a plate which includes inlet channel 44 which is mounted to the inside surface of frame 10 to connect the two deadspaces 26, 26' and to divert the air flow from ventilation opening 18 through the deadspaces 26, 26', with orbital cushions, if any, attached directly to the frame 10.

For the preferred embodiment, fasteners, such as, for example, screws 47, 47' are preferably used to attach ventilation liner 42 to the frame. Alternatively, any conventional means for mounting the ventilation liner 42 to the frame can be used such as, for example, adhesives for permanent mounting, or mechanical fasteners or clips or hook and pile type fasteners for removable mounting.

Figure 3:
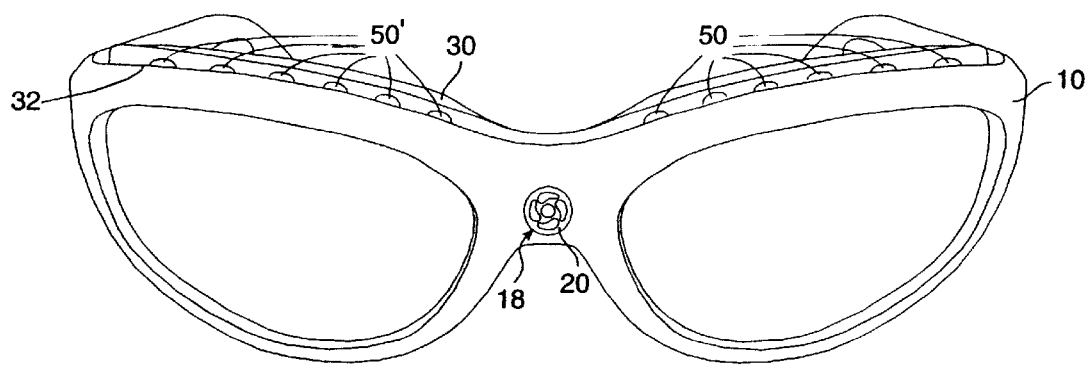
FIG. 3 is a front view of the eyewear of FIG. 1 without the cushion.
Figure 4:
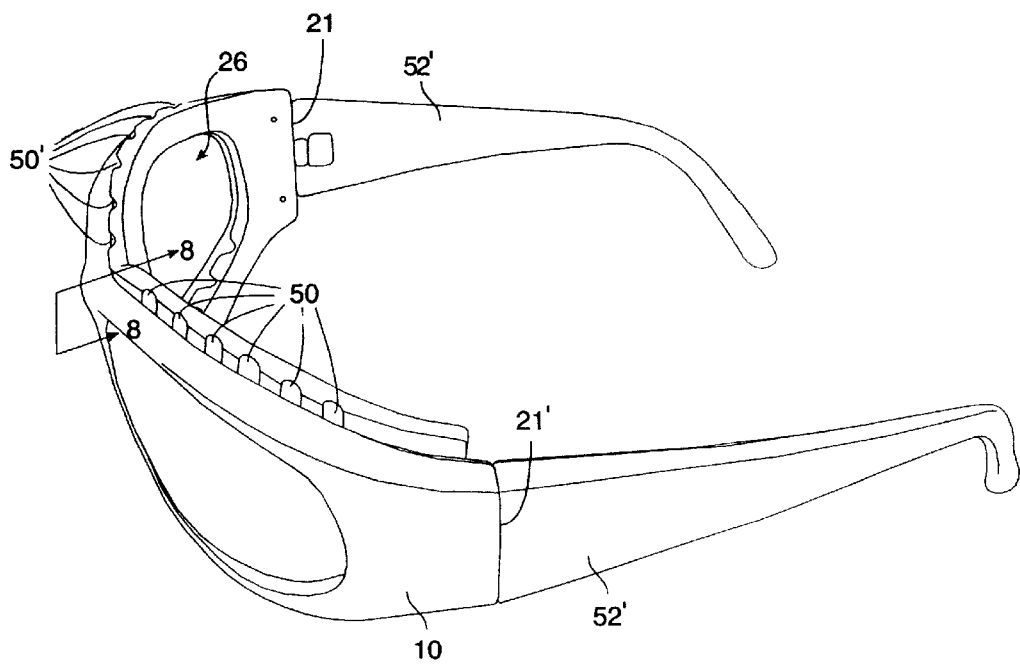
FIG. 4 is a side view of the eyewear of FIG. 1 without the cushion.
Figure 5:
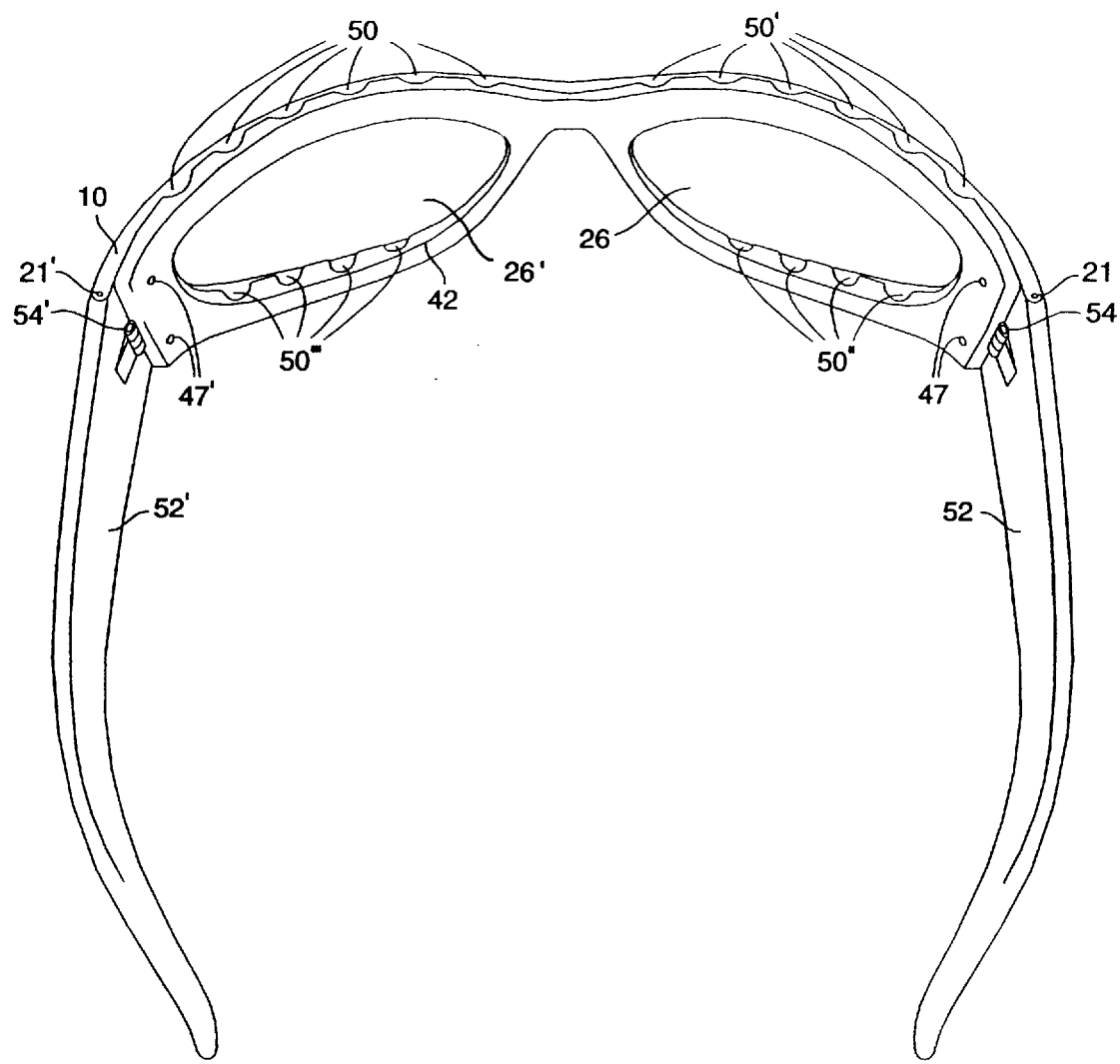
FIG. 5 is a perspective back view of the eyewear of FIG. 1 without the cushion.
Figure 6:
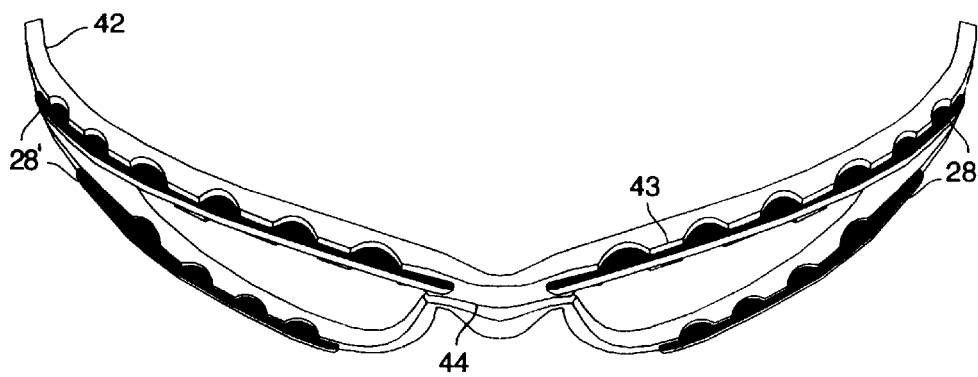
FIG. 6 is a perspective top view of a ventilation liner of the present invention showing filtering media in place.
Figure 7:
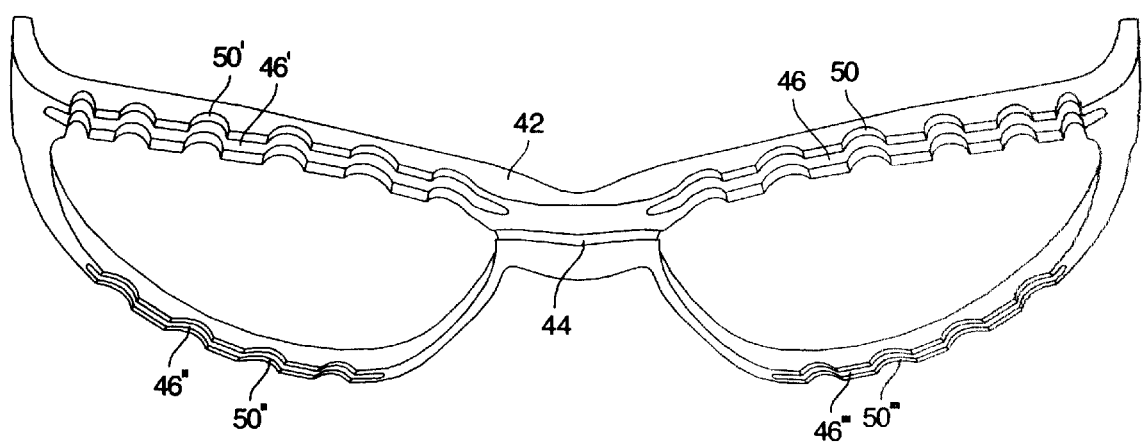
FIG. 7 is a front view of the ventilation liner of FIG. 6.

As shown most clearly in FIGS. 6 and 7, ventilation liner 42 can also be provided with a plurality of upper grooves 50, 50', lower grooves 50", 50'" which, in combination with inlet channel 44, provide dynamic ventilation in the assembled eyewear. As shown in FIGS. 3 and 4, ventilation liner 42 may be mounted to frame 10 so that the upper surface 30 of ventilation liner 42 extends slightly above the upper surface 32 of the frame 10. This provides a ventilated surface for catching and directing the wind through upper grooves 50, 50' down into the dead space 26 between the lenses and the eyes. To prevent particulate matter from being blown into the dead space, a filtering element 28 is preferably placed into each of channels 46, 46', 46", 46'", shown most clearly in FIGS. 6 and 7. Filtering element 28 can be any air-permeable material capable of effectively removing most particulate matter such as dust, sleet, and snow, but preferably is an air-permeable foam gasket formed to fit snugly inside the channels 46, 46', 46", 46'" and to obstruct grooves 50, 50', 50", 50'" so that air passing through grooves 50, 50', 50", 50'" must pass through a filter element 28. While it would be possible to eliminate channels 46, 46', 46", 46'" and simply place filtering elements in each individual groove 50, 50', 50", 50'", or to cover the exterior of the individual grooves 50, 50', 50", 50'" with a filtering cover, this is not preferred as it provides a greater obstruction to, and accordingly reduces, the airflow across the inner surface of each lens. In most instances, we prefer to use the smallest possible filtering element which will provide effective filtering, since this provides the least obstruction to the free flow of air through the deadspace and the smallest weight for the assembled eyewear.

Inlet channel 44 of ventilation liner 42 is positioned immediately behind the inlet opening 18 of frame 10 when ventilation liner 42 is mounted to the frame 10. While a filtering element could be placed in channel 44, it is preferably not. Channel 44 is preferably left unobstructed, with filtering of the airstream most preferably provided by a filter element 24 placed in inlet opening 18. As inlet channel 44 provides a channel for effective cross-flow of air between the dead spaces 26 in front of the user's eyes, it is present even if frame 10 is not provided with an inlet opening 18.

This arrangement provides for a dynamic flow of air in the preferred embodiment through both the inlet opening 18 and grooves 50, 50', the air through grooves 50, 50' being filtered preferably by a filter element 28, 28' placed in the channels 46, 46'. As the air passes through the filter element 24 in the inlet opening 18, it encounters channel 44, which directs the air flow into the dead space around each eye. This airflow will then encounter the filtered air from the grooves 50, 50', and the two airstreams can flow downwards across the inside surfaces of lenses 14, 14' and out through the grooves 50", 50'". Of course, the airflow through the dead space can change depending upon the position of the wearer's head, but remains effective in providing ventilation for the dead space. The dynamic movement of air through the deadspace 26 prevents a buildup of warm, moist air as the wearer engages in active sports which could otherwise produce fogging or discomfort.

Figure 2:
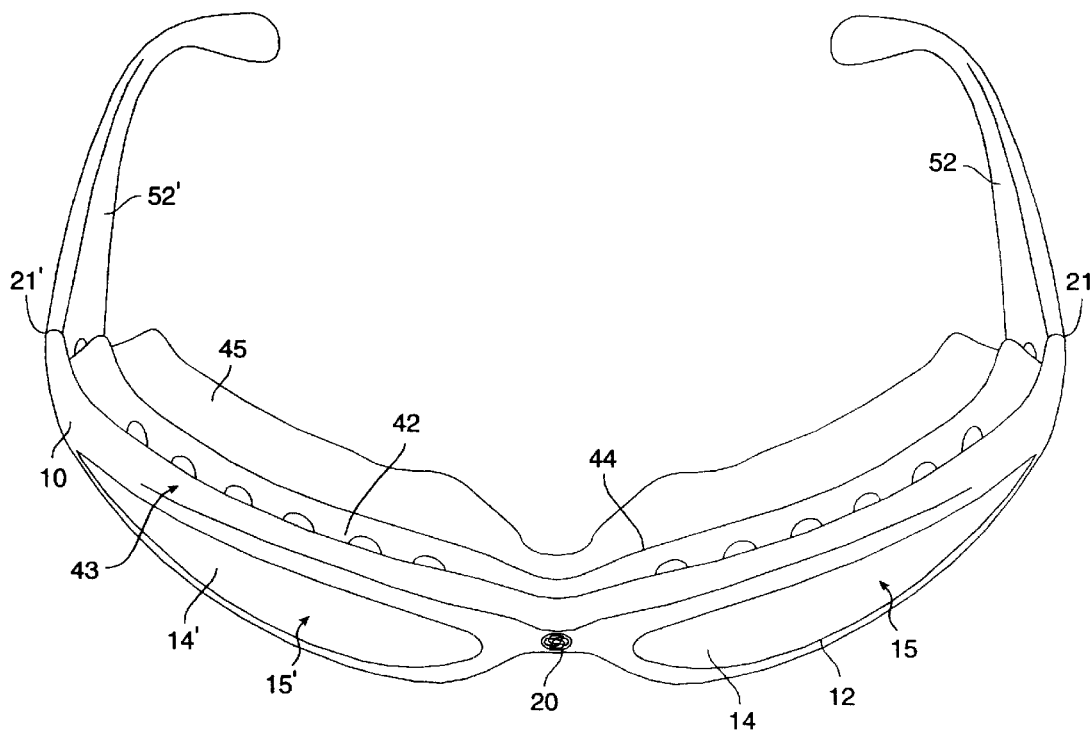
FIG. 2 is a perspective top view of the eyewear of FIG. 1.

A pair of temple bars 52, 52', shown in FIGS. 1 and 2, or an adjustable elastic strap 56 (as shown in U.S. Pat. No. 6,233,342, which has been incorporated herein by reference), can be conventionally used to support the frames 10 on the user's head. A surface 21, 21' at each end of the frame 10 is conventionally provided for connecting the temple bars 52, 52', or strap 56 to the frame. Temple bars 52, 52', are preferably connected conventionally to the surface 20, 20' to allow the bars 52, 52', to pivot around a hinge pin 54, 54' for selectively folding the bars 52, 52', to a closed position towards the inner surface of the frame or to an open position for mounting on the wearer's head in the well-known conventional fashion. Temple bars 52, 52', may be permanently mounted for such pivoting movement, or may be removably mounted using well-known, bayonet type mounts which allow for removal of the temple bars 52, 52', and replacement by a strap. Likewise, a strap may be permanently or removably mounted to the rear surface 21, 21'. The length of the strap can be conventionally adjusted using a buckle or other adjustment means to provide a snug fit against the wearer's face.

In use the present invention is particularly advantageous to users who wish to use sportsglasses for vigorous activities, such as skiing or riding motorcycles, snowmobiles or the like, which involve speed, and thus require both ventilation and protection against airborne particulate matter such as dust, sleet or snow. For vigorous activities involving speed, the user puts the sportsglasses on and begins the sports activity. As the user moves, air is directed through both ventilation opening 18 and through grooves 50, 50' where any particulate matter is trapped by filter elements 28, 28'. As the air passes through ventilation opening 18, it encounters channel 44 which splits the airstream in two, directing it to the right and the left across the inner surface of each lens, where it encounters the airstream flowing through upper ventilating grooves 50, 50'. This airflow alleviates any tendency to fog and constantly changes the air in the dead space to prevent a buildup of heat or humidity as the user exercises. Filtering elements are preferably also placed in channels 46", 46'" to prevent particulate matter being introduced into the deadspace through lower ventilating grooves 50", 50'".

One skilled in the art will recognize at once that it would be possible to construct the present invention from a variety of materials and in a variety of different ways. While the preferred embodiments have been described in detail, and shown in the accompanying drawings, it will be evident that various further modification are possible without departing from the scope of the invention as set forth in the appended claims.

What is claimed is:

1. Eyewear for use in sports and the like, comprising:
   a frame shaped to fit a wearer's face having an inner surface, an outer surface, a lens mounting surface for mounting a lens means for protecting a wearer's eyes, at least one lens mounted on said lens mounting surface, a nose bridge for supporting said frame on said wearer's face, and, a surface on each side of the frame for attaching a means for supporting the frame on the wearer's head;
   a ventilation liner mounted to the inner surface of said frame, said ventilation liner having an aperture of substantially the same size and shape as the lens mounting surface of the frame for providing a first deadspace between said lens and a first of said wearer's eyes and a second deadspace between said lens and a second of said wearer's eyes, said ventilation liner further having a front surface closely engaging the inner surface of said frame, said front surface including a plurality of filtered upper ventilation grooves for directing a flow of air through said first and second deadspace, said ventilation liner further including a channel connecting said first and said second deadspace for allowing air to flow between said first and said second deadspace, said ventilation liner further including filtered lower ventilation grooves for allowing air to flow through said first and said second deadspace, said ventilation liner further including a cushion mounted across a rear surface of said ventilation liner for engaging a wearer's skin around the wearer's eyes.

2. The eyewear of claim 1 additionally comprising a ventilation opening through a front surface of said frame, and wherein said channel of said ventilation liner is positioned to divert a flow of air from said ventilation opening in said frame into said first and said second deadspace.

3. The eyewear of claim 2 wherein ventilation opening includes a filter element.

4. The eyewear of claim 2 wherein said ventilation opening through said front surface of said frame is located in said nose bridge.

5. The eyewear of claim 4 wherein said ventilation opening is filtered to prevent the ingress of particulate matter by placing a filter element in said ventilation opening and covering an outside of said ventilation opening with a perforated vent cover to prevent loss of the filter element.

6. The eyewear of claim 5 wherein said filtering element is formed from air permeable foam.

7. The eyewear of claim 1 wherein said ventilation liner is mounted to extend above a top surface of said frame to expose said plurality of upper ventilation grooves on said front surface of said ventilation liner for directing a flow of air from said filtered upper ventilation grooves into said first and said second deadspace.

8. The eyewear of claim 1 wherein said cushion is formed from air permeable foam.

9. The eyewear of claim 1 wherein said ventilation liner includes a channel intersecting each said ventilating groove, said channel mounting a filter element for preventing the ingress of particulate matter into said deadspace through said ventilating grooves.

10. The eyewear of claim 1 wherein the lens mounting surface defines two apertures, one for each eye of a wearer.

11. The eyewear of claim 10 wherein each aperture is covered by a lens.

12. The eyewear of claim 1 wherein the lens mounting surface defines a single aperture for both eyes of a wearer, and said aperture is covered by a single lens.

13. The eyewear of claim 1 wherein said means for mounting the frame to the head of the wearer comprises a temple bar hingedly mounted at each end of said frame, said temple bar shaped to fit a user's head in a region above and behind the wearer's ears.

14. The eyewear of claim 1 wherein said means for mounting the frame to the head of the wearer comprises an elastic strap having a first and a second end, said first end removably mounted to a first end of said frame, and said second end removably mounted to a second end of said frame.

15. Eyewear for use in sports activities, comprising:
a frame shaped to fit a wearer's face, said frame having an inner surface, an outer surface, a pair of orbital openings for surrounding the eyes of a wearer, a nose bridge connecting said pair of orbital openings, said nose bridge including a ventilation opening, a lens mounting surface mounting a lens over each orbital opening, and a surface on each side of the frame for attaching a means for supporting the frame on the wearer's head; and a ventilation liner including a channel mounted to divert air flowing through said ventilation opening to the space located between each lens and said wearer's face.

16. The eyewear of claim 15 wherein said ventilation liner additionally includes a pair of orbital openings connected by a nose bridge of substantially the same size and shape as said orbital openings and nose bridge of said frame, a front surface mounted to closely engage the inner surface of said frame, a rear surface, a plurality of filtered upper ventilation grooves across an upper portion of the front surface of each orbital opening of said ventilation liner and a plurality of filtered lower ventilation grooves across a lower portion of the front surface of each orbital opening of said ventilation liner, and a cushion covering said rear surface of said ventilation liner for engaging a wearer's skin around the eyes, and wherein said channel is formed in said nose bridge of said ventilation liner in a position to be aligned with said ventilation opening of said frame for diverting an airflow from said ventilation opening across an inner surface of each said lens.

17. The eyewear of claim 16 wherein said cushion is formed from air permeable foam.

18. The eyewear of claim 16 wherein said upper and lower ventilation grooves are each intersected by a filter channel containing a filter element.

19. The eyewear of claim 18 wherein said filter channel substantially perpendicularly intersects said ventilation grooves.

20. The eyewear of claim 16 wherein a top surface of said ventilation liner extends above a top surface of said frame, whereby said upper ventilation grooves of said ventilation liner are exposed to an airflow against the wearer's face, creating in conjunction with the airflow through the ventilation opening in the nosebridge, an airflow across a rear surface of each said lens which passes through said bottom ventilation grooves.

21. The eyewear of claim 15 wherein said means for mounting the frame to the head of the wearer comprises a temple bar hingedly mounted to the each said surface of each side of said frame, said temple bar shaped to fit the wearer's head in a region above and behind a wearer's ears.

22. The eyewear of claim 15 wherein said means for mounting the frame to the head of the wearer comprises an elastic strap having a first and a second end, said first end mounted to a first surface at one side of said frame, and said second end mounted to a second surface at an opposite side of said frame.

23. The eyewear of claim 15 wherein said ventilation opening in said nose bridge is filtered by placing a filter element within said ventilation opening.

24. The eyewear of claim 23 wherein said ventilation opening is covered by a perforated vent cover to prevent loss of said filter element.

* * * * *